(12) United States Patent
Yano et al.

(10) Patent No.: US 6,645,594 B1
(45) Date of Patent: Nov. 11, 2003

(54) FORMAZAN METAL COMPLEX

(75) Inventors: Kentaro Yano, Okayama (JP); Katsumi Orita, Okayama (JP); Toshio Kawata, Okayama (JP); Shigeo Yasui, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/762,535

(22) PCT Filed: Jan. 6, 2000

(86) PCT No.: PCT/JP00/03565

§ 371 (c)(1),
(2), (4) Date: Feb. 8, 2001

(87) PCT Pub. No.: WO00/75111

PCT Pub. Date: Dec. 14, 2000

(30) Foreign Application Priority Data

Jun. 9, 1999 (JP) .............................. 11-163036
May 17, 2000 (JP) ....................... 2000-145313

(51) Int. Cl.[7] .................................. B32B 3/02
(52) U.S. Cl. ................ 428/64.1; 428/64.8; 430/270.14
(58) Field of Search .............................. 428/64.1, 64.4, 428/64.8, 913; 430/270.14, 270.16, 495.1, 945; 369/283, 288

(56) References Cited

U.S. PATENT DOCUMENTS 5,547,728 A * 8/1996 Cunningham ............... 428/64.1
5,695,843 A * 12/1997 Chapman .................... 428/64.1
5,731,054 A * 3/1998 Chapman .................... 428/64.1
5,773,193 A * 6/1998 Chapman ................. 430/270.16
5,922,429 A * 7/1999 Chapman .................... 428/64.1

FOREIGN PATENT DOCUMENTS

| JP | 59-48189 | * 3/1984 |
| JP | 60 122195 | 6/1985 |
| JP | 10 337958 | 12/1998 |
| WO | 01 19923 | 3/2001 |

OTHER PUBLICATIONS

Chemical Abstracts, vol. 108, No. 14, "Complexation of 5–Br–PNPFF '1–(5'–bromo–2'–pyridyl)–5–(4'–nitrophenyl)–3–(2'–furyl) formazan! with cadmium and its application", (1988).

Chemical Abstracts, vol. 105, No. 16, "Study of spectrophotometric determination of microamounts of copper with 5–Br–PPFF '–(5–bromo–2–pyridyl)–5–phenyl–3–(2–furyl) formazan!", (1986).

* cited by examiner

Primary Examiner—Elizabeth Mulvaney
(74) Attorney, Agent, or Firm—Browdy and Neimark, P.L.L.C.

(57) ABSTRACT

The present invention provides organic compounds which improve the light resistance of organic dye compounds without substantially deteriorating their preferable light properties when applied to them, and have satisfactory solubility in organic solvents and compatibility with organic dye compounds. The object of the present invention is solved by formazan metal compounds which comprise specific formazan compounds as ligands; process thereof; light-resistant improvers, optical recording media, and light absorbents, which all comprise the formazan metal complexes; and formazan compounds as intermediates for producing the formazan metal complexes

11 Claims, 3 Drawing Sheets

FORMAZAN METAL COMPLEX

The present application is the national stage under 35 U.S.C. 371 of PCT/JP00/03565, filed Jan. 6, 2000.

TECHNICAL FIELD

The present invention relates to organic metal complexes, and more particularly, to novel formazan metal complexes which are useful as light-resistant improvers for light absorbents and organic dye compounds.

BACKGROUND ART

As a new development in the fields of information recordings and displays, the following organic dye compounds are being rapidly increased in their demand: For example, in the former field, organic dye compounds having laser action or sensitivity to laser beams; and in the latter field, organic dye compounds having electroluminescence ability as well as those having laser action. In these days called an information technology era which requires improvement of the performance of information recording and displaying means, magnification of recording-capacity, downsizing, and satisfactory storage-stability, it has been more increased in demand for organic dye compounds having superior optical properties than the past, and this results in a development of a diversified organic dye compounds one after another. Organic dye compounds, however, have relatively-low light resistance as a whole and change in themselves to lose their inherent properties when exposed with light or allowed to illuminate repeatedly. For example, polymethine dyes, which are frequently used in optical recording media such as CD-Rs (a write-once memory using compact disc) and digital versatile disc recordable (DVD-R, a write-once memory using digital video disc) that are all highlighted as high-density information recording media, are susceptibly oxidized and decomposed by singlet oxygen, generated when the polymethine chains are exposed with reading and environmental lights. Since optical recording media are required to have at least 10 years of shelf-life, and therefore, to attain the requirement in this field, the research for light-resistant improvers applied for organic dye compounds is most energetically carried out.

To solve the problem of polymethine dyes, there has been proposed a light-resistant improver comprising a formazan metal complex. The formazan metal complexes as proposed in Japanese Patent Kokai Nos. 295,079/96, 151,863/98, and 337,958/98 are effective in improving the light resistance of polymethine dyes, however, they have the following problems: Since they have relatively-low solubility in organic solvents, which are used frequently in preparing optical recording media, and have insufficient compatibility with dyes, the processibility and the product yield may be lowered due to the crystallization of the polymethine dyes and metal complexes when the light-resistant improvers are added in an amount up to a level of sufficiently improving the light resistance of the dyes in preparing optical recording media, while the desired properties and features of the final products could be hardly attained when the amount of light-resistant improvers is set to a relatively-low level.

OBJECT OF THE INVENTION

In view of the foregoing, the object of the present invention is to provide formazan metal complexes, which have satisfactory solubility in organic solvents and compatibility with dyes, and which can be applicable to organic dye compounds and improve their light resistance without substantially deteriorating their preferable light properties. The term "organic dye compounds" as referred to in the present invention means organic dye compounds in general having sensitivity to light, and significantly relates, for example, to polymethine dyes such as cyanine dyes.

The energetic study and screening of the present inventors found that, when applied to organic dye compounds including polymethine dyes, formazan metal complexes, which have as ligands formazan compounds having a pyridine ring at the C-5 of formazan skeleton and having either a pyridine ring, furan ring, or straight or branched alkyl group at the C-3 of formazan skeleton, or which have tautomers of the formazan compounds, can improve the light resistance without substantially deteriorating the desired light-properties of the organic dye compounds and effectively inhibit the undesirable changes such as deterioration, fading, discoloration, and denaturation due to the exposure of reading and environmental lights. They also found that the formazan metal complexes of the present invention neither crystallize in themselves nor reduce the solubility of organic dye compounds even when applied to the compounds at a relatively-high concentration because the formazan metal complexes have relatively-high solubility in organic solvents and satisfactory compatibility with organic dye compounds. The present invention was made based on the creation of the novel formazan metal complexes and the finding of their industrially-useful features.

BRIEF EXPLANATION OF THE ACCOMPANYING DRAWINGS

BEST MODE OF THE INVENTION

Figure 1:
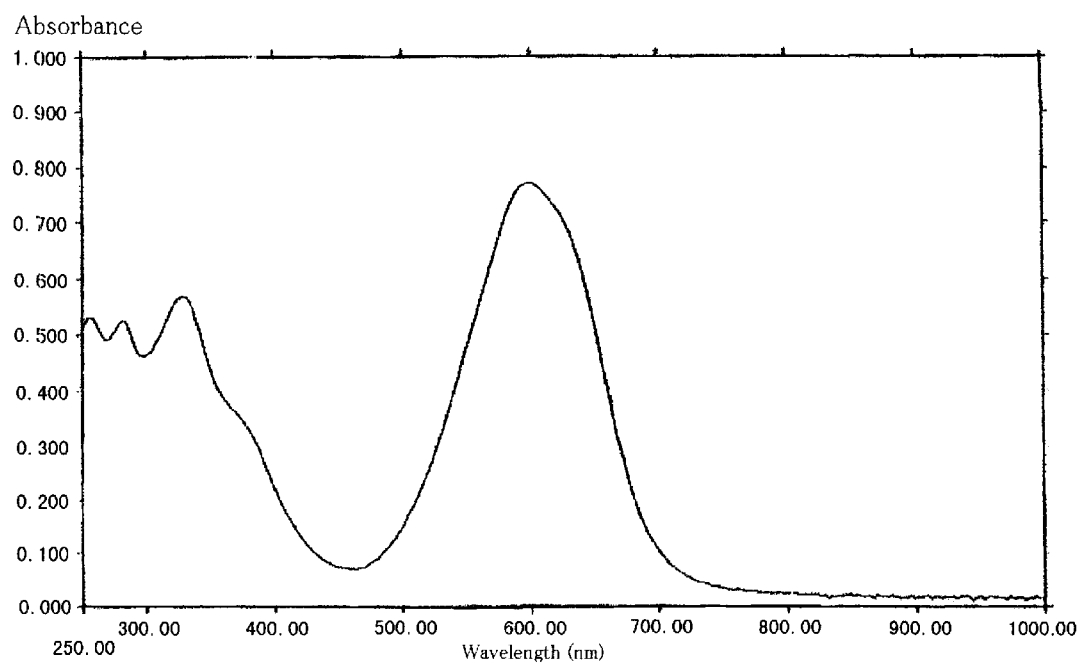
FIG. 1 is an absorption spectrum of one of the formazan metal complexes according to the present invention.

The present invention solves the above object by providing formazan metal complexes which have as ligands formazan compounds represented by Formula 1 or tautomers thereof:

Formula 1:

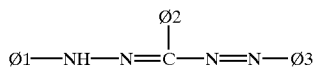

In Formula 1, ϕ1 represents a pyridine ring which may have, for example, a halogen such as chlorine, bromine or iodine; an alkoxy group such as methoxy, ethoxy, propoxy, isopropoxy, butoxy, or tert-butoxy group; nitro, cyano, carboxy, carboxylicester, carboxylic amide, sulfonyl, or sulfonic ester group; a sulfonic amide group composed of sulfonic acid, for example, with a primary or secondary amine which may have a ring structure such as morpholine, piperazine, piperidine, or cyclohexylamine; and one or more of the same or different substituents such as straight, cyclic or branched alkyl groups having usually up to 18 carbon atoms, preferably, 1 to 10 carbon atoms, for example, methyl, ethyl, propyl, isopropyl, butyl, sec-butyl, tert-butyl, isobutyl, pentyl, tert-pentyl, isopentyl, neopentyl, 1-methylpentyl, 2-methylpentyl, 5-methylpentyl, hexyl, isohexyl, cyclohexyl, heptyl, octyl, and decyl groups.

In Formula 1, φ2 represents a pyridine ring, furan ring or straight or branched alkyl group, where the pyridine and furan rings may have one or more substituents similarly as in φ1. The alkyl groups in φ2 are generally selected, for example, from short-length alkyl groups having 1 to 5 carbon atoms such as methyl, ethyl, propyl, isopropyl, butyl, isobutyl, sec-butyl, tert-butyl, pentyl, isopentyl, neopentyl, and tert-pentyl groups.

Throughout φ1 and φ2, when the substituents in the pyridine and/or furan rings are alkyl groups, one or more of the hydrogen atoms in the alkyl groups may be substituted with halogens and/or hydroxy group or with alkyl groups similarly as in φ1 via oxy, thio or nitrilo group. In the latter, examples of alkyl groups substituted via oxy group include methoxymethyl, methoxyethyl, ethoxyethyl, butoxyethyl, ethoxyethoxyethyl, phenoxyethyl, methoxypropyl, and ethoxypropyl groups; examples of alkyl groups substituted via thio group include methylthioethyl, ethylthioethyl, ethylthiopropyl, phenylthioethyl, and methylsulfonylethyl groups; and examples of alkyl groups substitutedvianitrilo group include dimethylaminoethyl, diethylaminoethyl, dimethylaminopropyl, and diethylaminopropyl groups.

In Formula 1, φ3 represents an aromatic ring, and usually it can be selected from monovalent groups of monocyclic or polycyclic aromatic compounds such as phenyl, naphthyl, anthracenyl, imidazolyl, benzoimidazolyl, pyridyl, pyrazinyl, pyrimidinyl, pyridazinyl, piperidinyl, thiazolyl, benzothiazolyl, quinolyl, isoquinolyl, and benzoxazolyl groups. These aromatic rings may have one or more of the same or different substituents, and respective examples of which are halogens such as fluorine, chlorine, bromine, and iodine; alkoxy groups such as methoxy, ethoxy, propoxy, isopropoxy, butoxy, and tert-butoxy groups; amino groups such as dimethylamino, diethylamino, and p-methoxyphenylamino groups; nitro, cyano, carboxy, carboxylic ester, carboxylic amide, and sulfonic ester groups; sulfonic amides which are composed of sulfonic acid, for example, with primary or secondary amines which may have a ring structure such as morpholine, piperazine, piperidine, or cyclohexylamine; and straight, cyclic or branched alkyl groups having usually up to 18 carbon atoms, preferably, 1 to 10 carbon atoms, for example, methyl, ethyl, propyl, isopropyl, butyl, sec-butyl, tert-butyl, isobutyl, pentyl, tert-pentyl, isopentyl, neopentyl, 1-methylpentyl, 2-methylpentyl, 5-methylpentyl, hexyl, isohexyl, cyclohexyl, heptyl, octyl, and decyl groups. When the substituents are alkyl groups, one or more of the hydrogen atoms in the alkyl groups may be substituted with halogens and/or hydroxy group or with alkyl groups similarly as in φ1 via oxy, thio or nitrilo group. Since the formazan metal complexes, which φ3 is phenyl group having a plural alkoxy groups, have relatively-high light-resistance-improving-ability and relatively-higher solubility in organic solvents which are frequently used in preparing optical recording media, they have the actual merit of effectively improving the working efficiency in preparing optical recording media. The hydrogen atom in the imino group of formazan compounds is migratory in general, and thus, among formazan compounds represented by Formula 1 in which φ1 and φ3 each have a different unsymmetrical structure, meaning that there exist two tautomers theoretically. The term formazan compounds as referred to in the present invention includes all these tautomers unless specified otherwise. When the formazan compounds of the present invention exist in an equilibrated mixture of these tautomers, they may be only expressed with either of their tautomers according to usual manner in this field, unless need arises.

The formazan metal complexes of the present invention are those which are composed of one or more of the above formazan compounds or their tautomers that coordinate metals as central atoms. The metals as central atoms are generally metal elements of the 3 to 10 groups in the periodic law table: For example, those in the form of an atom, oxide, and halide such as fluoride, chloride, bromide, and iodide. Respective examples of the metal elements are, for example, scandium, yttrium, titanium, zirconium, hafnium, vanadium, niobium, tantalum, chromium, molybdenum, tungsten, manganese, technetium, rhenium iron, cobalt, nickel, rubidium, palladium, osmium, iridium, platinum,copper,silver,gold,zinc,cadmium, and mercury. In general, nickel, zinc, cobalt, iron, copper and palladium are frequently used from a view point of their cost and easiness of availability.

Preferable ones are formazan metal complexes having a divalent metal (M) as a central atom, particularly, the complexes represented by Formula 2. In Formula 2, Fz represents a formazan compound represented by Formula 1 or its tautomer, and m is the number of formazan compounds or their tautomers as ligands (Fz) that coordinate M, and usually it is 1 or 2. X is an appropriate counter ion, and n is the number of X to keep the equivalence of electric charge in the complexes. The formazan metal complexes of the present invention usually have an electric charge of −2, 0 or 1. When the electric charge is 0, n is zero, meaning that there exists no X. Examples of the counter ion X are the following ions; anions such as phosphoric acid hexafluoride, fluoric acid ion, hydrochloric acid ion, bromic acid ion, iodic acid ion, phosphoric acid ion, perchloric acid ion, periodic acid ion, antimony hexafluoride ion, tin acid hexafluoride ion, fluoroboric acid ion, tetrafluoroborate ion, thiocyanic acid ion, benzenesulfonic acid ion, naphthalenesulfonic acid ion, benzenecarboxylic acid ion, alkylcarboxylic acid ion, trihaloalkylcarboxylic acid ion, alkylsulfonic acid ion, trihaloalkylsulfonic acid ion, and nicotinic acid ion; and cations such as ammonium ion, and tetraalkylammonium ion.

Formula 2:

Examples of the ligands in the formazan metal complexes of the present invention include the formazan compounds represented by Chemical Formulae 1 to 41 and tautomers thereof:

Chemical Formula 1:

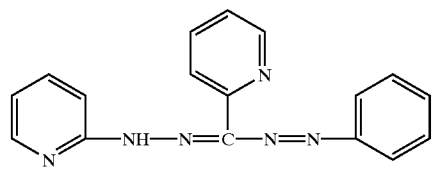

Chemical Formula 2:
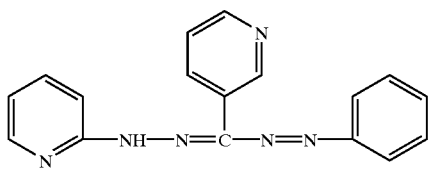
Chemical Formula 3:
Chemical Formula 4:
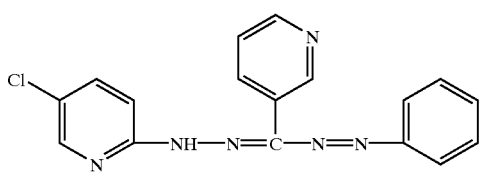
Chemical Formula 5:
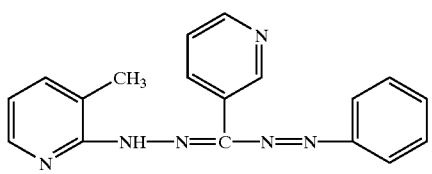
Chemical Formula 6:
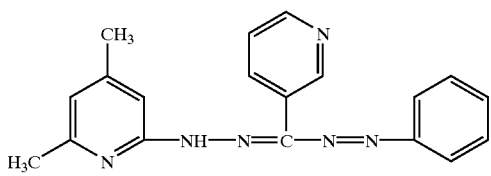
Chemical Formula 7:
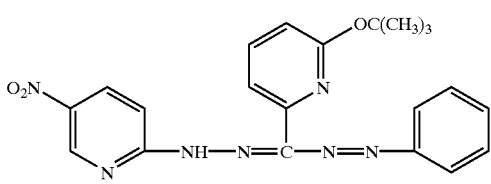
Chemical Formula 8:
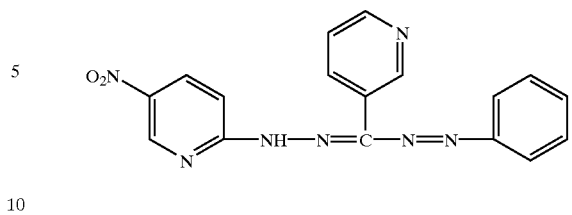
Chemical Formula 9:
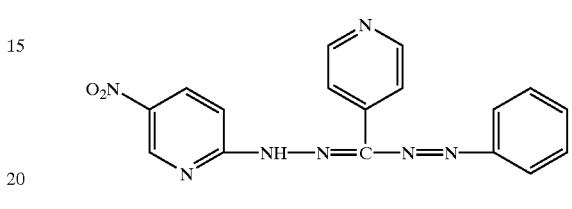
Chemical Formula 10:
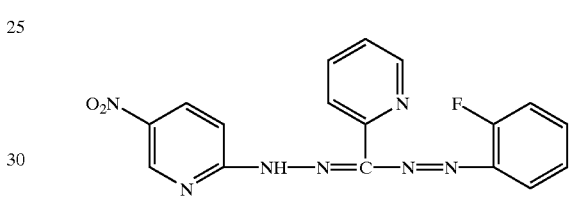
Chemical Formula 11:
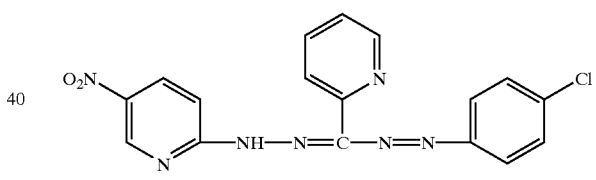
Chemical Formula 12:
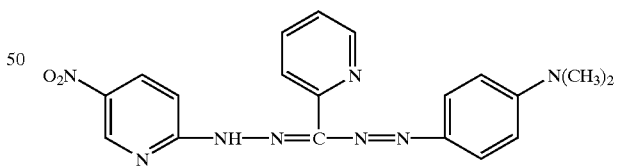
Chemical Formula 13:
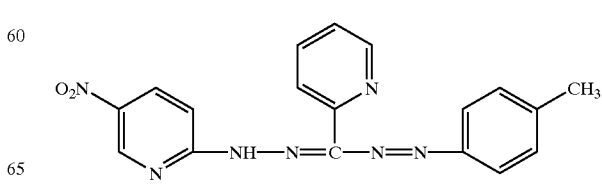

Chemical Formula 14:
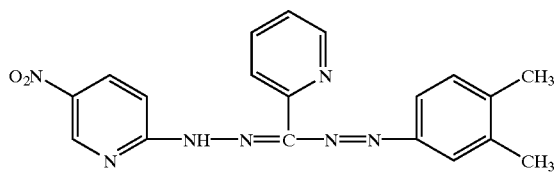
Chemical Formula 15:
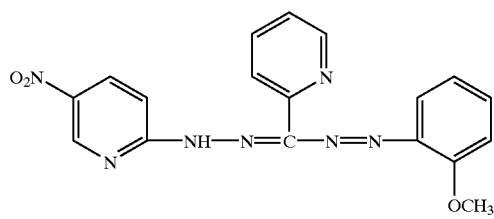
Chemical Formula 16:
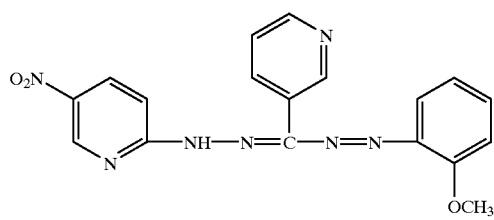
Chemical Formula 17:
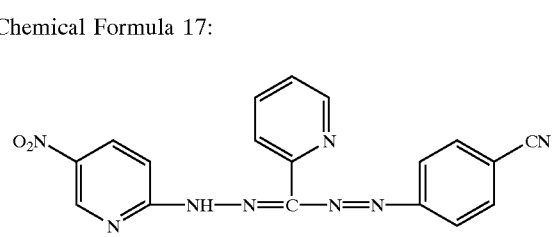
Chemical Formula 18:
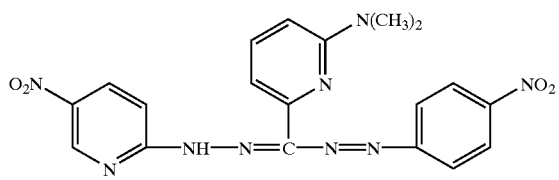
Chemical Formula 19:
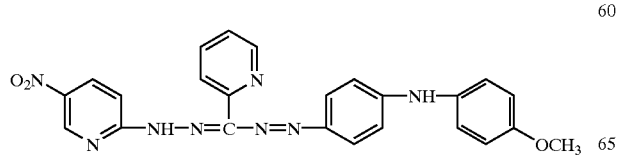
Chemical Formula 20:
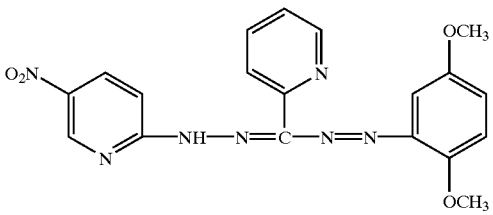
Chemical Formula 21:
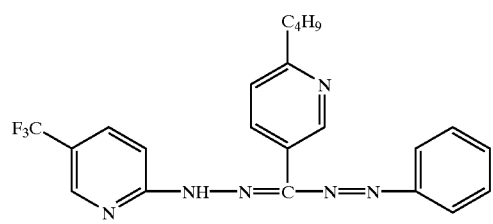
Chemical Formula 22:
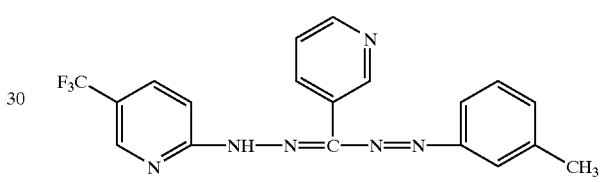
Chemical Formula 23:
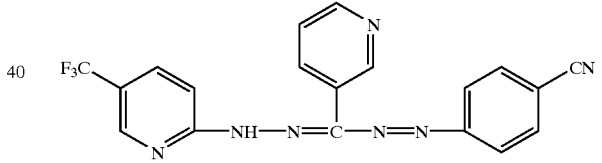
Chemical Formula 24:
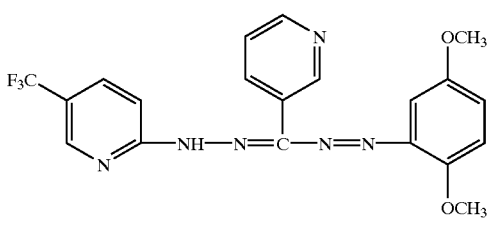
Chemical Formula 25:

Chemical Formula 26:
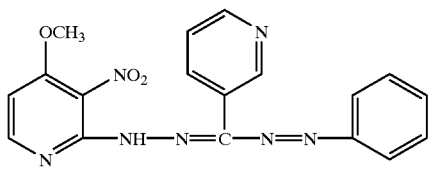
Chemical Formula 27:
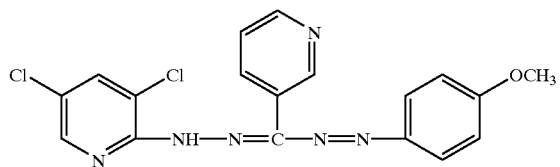
Chemical Formula 28:
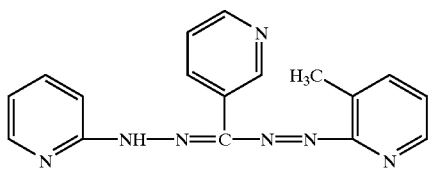
Chemical Formula 29:
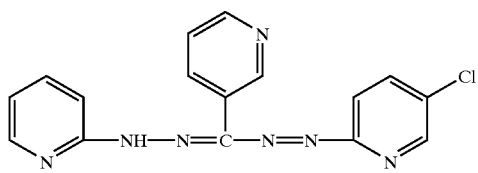
Chemical Formula 30:
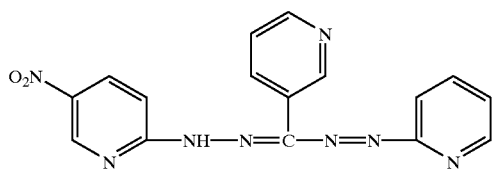
Chemical Formula 31:
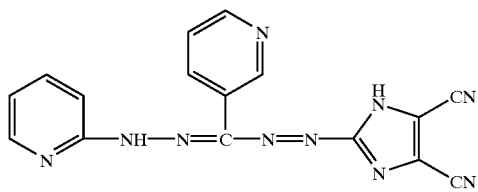
Chemical Formula 32:
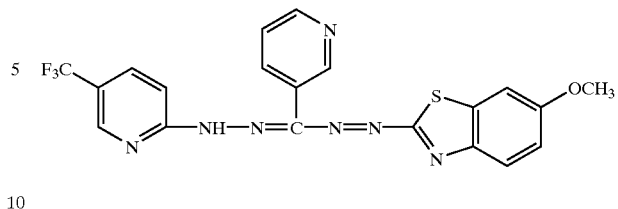
Chemical Formula 33:
Chemical Formula 34:
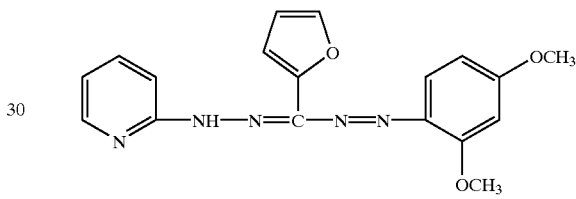
Chemical Formula 35:
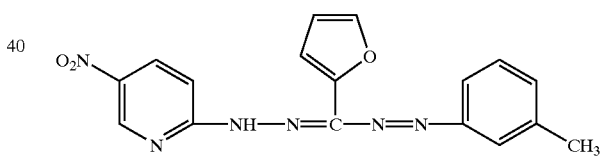
Chemical Formula 36:
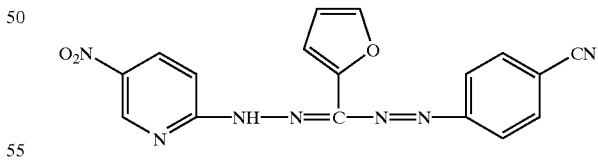
Chemical Formula 37:
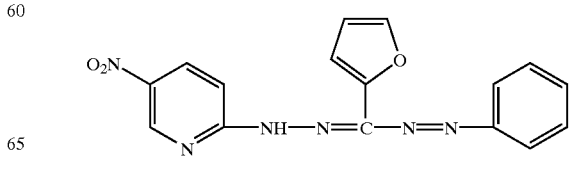

Chemical Formula 38:

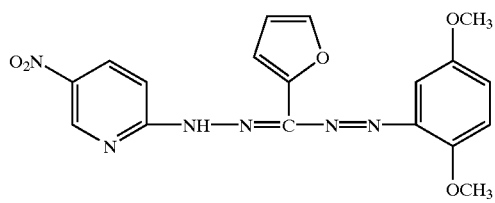

Chemical Formula 39:

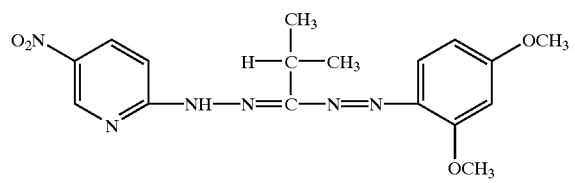

Chemical Formula 40:

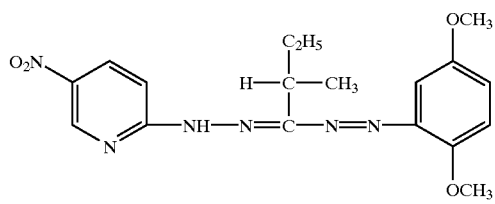

Chemical Formula 41:

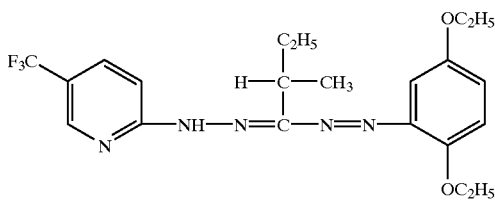

The formazan metal complexes of the present invention can be prepared, for example, in accordance with the methods as disclosed in "*Analytical Sciences*", by Akira Uchiumi, Vol. 7, pp. 119–124 (1991), "*Analytical Sciences*", by Akira Uchiumi, Vol. 7, pp. 459–462 (1991), "*Bunseki-Kagaku*" (*Analytical Chemistry*) by Akira Kawase, Vol. 16, pp. 1,364–1,369 (1967), and Japanese Patent Kokai No. 144, 997/87. With an economical viewpoint, advantageously usable methods are those which use as intermediates the formazan compounds represented by Formula 1 or tautomers thereof, and produce the formazan metal complexes through a step of reacting the formazan compounds with appropriate metal salts. For example, the formazan compounds represented by Formula 1 are allowed to dissolve, for example, in non-aqueous solvents such as methanol, ethanol, 1,4-dioxane, acetone, acetonitrile, tetrahydrofuran, tetrahydropyran, formamide, N-methylformamide, N,N-dimethylformamide, dimethylsulfoxide, or mixtures thereof, while the appropriate metal salts are dissolved in a small amount of water or in mixture solutions of water and non-aqueous solvents, and the resulting solutions were added to the above solutions containing the formazan compounds, then allowed to react under stirring conditions. Varied depending on the desired formazan metal complexes, the above reaction usually completes within 10 hours when carried out at over ambient temperature but below a temperature of 100° C. In general, the metal salts usable in the present invention include their acetates, chlorides, and perchlorates. Respective examples of which are, for example, nickel acetate tetrahydrate, copper acetate anhydride, nickel chloride hexahydrate, cupric chloride dehydrate, cobalt chloride hexahydrate, ferrous chloride anhydride, nickel perchlorate hexahydrate, and copper perchlorate hexahydrate. All the formazan compounds represented by Chemical Formulae 1 to 41 can be easily converted into formazan metal complexes by the above methods. In the case of the formazan metal complexes having nickel as a central atom, it can be estimated that the formazan compounds bind to nickel as shown in Chemical Formula 3. In Chemical Formula 3, the solid line that connects the central atom M with nitrogen atom shows a covalent bond, and the broken line shows a coordinate bond.

Chemical Formula 3:

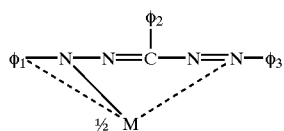

The formazan metal complexes of the present invention thus obtained may be used intact in a reaction mixture form depending on their use, and prior to use, they can be usually purified, for example, by conventional methods in general such as dissolution, separation, slanting, extraction, filtration, concentration, thin-layer chromatography, column chromatography, gas chromatography, high-performance liquid chromatography, distillation, crystallization, and sublimation which are used for purifying related compounds, and if necessary they can be used in combination. In the case of using as light-resistant improvers the formazan metal complexes of the present invention, for example, in optical recording media, dye lasers, and silver prints as light-resistant improvers or in solar batteries as optical absorbents, they should preferably be purified by the methods such as distillation, crystallization and/or sublimation, prior to use.

When used organic dye compounds including polymethine dyes, the formazan metal complexes of the present invention improve the light resistance of the organic dye compounds without substantially deteriorating their preferable light properties and effectively inhibit the undesirable changes such as deterioration, fading, discoloration, and denaturation of the dyes which are induced by the exposure of environmental light such as natural and artificial lights. Thus, the formazan metal complexes of the present invention have a variety of advantageous uses as light-resistant improvers of organic dye compounds in the fields that dislike undesirable changes of organic dye compounds induced by environmental light. In addition, most of the formazan metal complexes of the present invention have relatively-high compatibility with polymethine dyes such as cyanine dyes, and have strongly-higher solubility in organic solvents such as 2,2,3,3-tetrafluoro-1-propanol (abbreviated as "TFP" hereinafter), ethyl cellosolve, and diacetone alcohol than conventionally known formazan metal complexes. For example, when measured at 20° C. in ethyl cellosolve which is expected for use as a satisfactory organic solvent in the field of optical recording media, most of the formazan metal complexes of the present invention have solubility as high as 2 mg/ml or higher, and particular ones have solubility as high as 20 mg/ml or higher.

Accordingly, the fields to which the light-resistant improvers of the present invention are most advantageously applicable are, for example, those of optical recording media such as CD-Rs and DVD-Rs. When applied to polymethine dyes having an amidinium ion chromophore and being frequently used in the above optical recording media, more particularly, to cyanine dyes in which independently-separated two basic-heterocycles are bound together in such a manner that they each include the nitrogen termini of the amidinium ion chromophore, the light-resistant improvers of the present invention can effectively improve the light resistance of these dyes without substantially deteriorating their light properties required of optical recording media. Therefore, the optical recording media, which comprise the polymethine dyes such as cyanine dyes and the formazan metal complexes as light-resistant improvers for organic dye compounds, have advantageous features that they substantially do not cause error when reading information because the reflectance of unrecorded part on the recording surface of the optical recording media does not substantially lower even when repeatedly exposed with light during the reading of recorded information. Using the light-resistant improver of the present invention, the selectivity of polymethine dyes used for optical recording media can be extensively widened because the light-resistant improvers of the present invention are effective for both polymethine dyes, which have absorption maxima in the region of near infrared ray and which are recognized to be most easily decomposed by the exposure of light, and other polymethine dyes having their absorption maxima in a blue color region with shorter wavelengths. In addition, since the formazan metal complexes of the present invention have similar wavelengths as of the absorption maxima of indolenine pentamethine cyanine dyes, which are used frequently in CD-Rs, or have both absorption maxima in a shorter wavelength region nearness to the above wavelengths and relatively-high molecular extinction coefficients (maybe abbreviated as "$\epsilon$" hereinafter) in the absorption maxima, they can completely supplement satisfactory light-absorbency to the cyanine dyes without lowering the reflection properties of the dyes.

Explaining the method for use in optical recording media in relation to the use of the light-resistant improver of the present invention, since the light-resistant improvers do not need any specific treatment and handling when used in optical recording media, it can be prepared in accordance with conventional optical recording media; To control the light reflectance and the absorptance in recording layers, one or more organic dye compounds as light absorbents can be used in combination. If necessary, one or more of commonly used binders, dispersants, flame retardants, lubricants, anti-static agents, surfactants, and plasticizers can be mixed with an effective amount of the light-resistant improver(s) of the present invention, and then the resulting mixtures are dissolved in organic solvents. The resulting solutions are homogeneously coated on either side of substrates, for example, by the methods such as spraying, soaking, roller coating, and rotary coating, followed by drying the coated solution to form as a recording layer a thin layer of organic dye compound(s), and optionally forming a reflection layer, that is attached closely to the recording layer, made of a metal such as gold, silver, copper, platinum, aluminum, cobalt, zinc, nickel, iron, chromium, or an alloy thereof, for example, by vacuum deposition, chemical deposition, spattering, or ion-plating method; and/or sequentially coating an ultraviolet-ray hardening resin on the recording layer and hardening the coated resin by irradiating light to form a protection layer to be closely attached to the above reflection layer for protecting the recording layer from scratches, dusts, stains, etc.

The organic dye compounds used in the present invention generally include cyanine dyes which to both ends of a polymethine chain consisting of up to nine, preferably, one to seven methine groups are bound the same or different cyclic cores such as imidazoline, imidazole, benzimidazole, á-naphthoimidazole, â-naphthoimidazole, indole, isoindole, indolenine, isoindolenine, benzindolenine, pyridinoindolenine, oxazoline, oxazole, isoxazole, benzoxazole, pyridineoxazole, á-naphthoxazole, â-naphthoxazole, selenazoline, selenazole, benzoselenazole, á-naphthoselenazole, â-naphthoselenazole, thiazoline, thiazole, isothiazole, benzothiazole, á-naphthothiazole, â-naphthothiazole, tellulazoline, tellulazole, benzotellulazole, á-naphthotellulazole, â-naphthotellulazole, aquaridine, anthracene, isoquinoline, isopyrrole, imidaquinoxaline, indandione, indazole, indoline, oxadiazole, carbazole, xanthene, quinazoline, quinoxaline, quinoline, chroman, cyclohexanedione, cyclopentanedione, cinnoline, thiodiazole, thiooxazolidone, thiophene, thionaphthene, thiobarbituric acid, thiohydantoin, tetrazole, triazine, naphthalene, naphthyridine, piperazine, pyrazine, pyrazole, pyrazoline, pyrazolidine, pyrozolone, pyran, pyridine, pyridazine, pyrimidine, pyrylium, pyrrolidine, pyrroline, pyrrole, phenazine, phenanthridine, phenanthrene, phenanthroline, phthalazine, pteridine, furazan, furan, purine, benzene, benzoxazine, benzopyran, morpholine, and rhodanine rings; polymethine dyes such as merocyanine dyes, oxanol dyes, styryl dyes, azulenium dyes, squarylium dyes, pyrilium dyes, thiopyrylium dyes, and phenanthrene dyes; and other compounds such as acridine, azaannulene, azo metal complex, anthraquinone, indigo, indanthrene, oxazine, xanthene, dioxazine, thiazine, thioindigo, tetrapyraporphyradine, triphenylmethane, triphenothiazine, napthoquinone, phthalocyanine, benzoquinone, benzopyran, benzofuranone, porphyrin, and rhodamine dyes, which all can be appropriately used in combination, depending on use. Preferable organic dye compounds usable in combination with the formazan metal complexes of the present invention are those which have absorption maxima in a visible region, particularly, absorption maxima at wavelengths of 400–850 nm when in a thin layer form.

In the case of the organic dye compounds are polymethine dyes, the anions thereof can be appropriately selected depending on their solubility. Examples of such dyes are generally inorganic acid anions such as fluoric, chloric, bromic, iodic, perchloric, periodic, phosphoric acid hexafluoride, antimony hexafluoride, tin acid hexafluoride, phosphoric acid, fluoroboric acid, and tetrafluoroborate ions; organic acid anions such as thiocyanic acid, benzenesulfonic acid, naphthalenesulfonic acid, p-toluenesulfonic acid, alkylsulfonic acid, benzenecarboxylic acid, alkylcarboxylic acid, trihaloalkylcarboxylic acid, alkylsulfonic acid, trihaloalkylsulfonic acid, and nicotinic acid ions; and organic metal complex anions such as those of azo, bisphenyldithiol, thiocatecholchelate, thiobisphenolatechelate, and bisdiol-á-diketone.

When used as light-resistant improvers, the light-resistant improvers of the present invention can be used alone or, if necessary, in combination with one or more conventional light-resistant improvers within an amount that fulfills the object of the present invention. Examples of the conventional light-resistant improvers include nitroso compounds such as nitrosodiphenylamine, nitrosoaniline, nitrosophenol, and nitrosonaphthol; and metal complexes such as tetracyano-p-quinodimethane compounds, diimmonium salts, "NKX-1199" (bis[2'-chloro-3-methoxy-4-(2-methoxyethoxy)dithiobenzyl]nickel) produced by Hayashibara Biochemical Laboratories, Inc., Okayama, Japan, azo metal complexes, and phenylpyridylamine derivatives as disclosed in Japanese Patent Application No. 88,983/99, titled "Phenylpyridylamine derivatives" applied for by the same applicant as the present invention. As a composition ratio, 0.001–10 moles, and preferably 0.005–5 moles of the light-resistant improver(s) of the present invention with respect to the amount as the formazan metal complex(es) are incorporated into one mole of an organic dye compound as a light absorbent while increasing and decreasing the ratio. Depending on the kinds of the organic dye compounds, they are ineffective in exerting light-resistance improvement when used in a ratio below the above range, while the color concentration of them may lower when used in a ratio over the above range. Accordingly, in general, organic dye compounds and the light-resistant improvers of the present invention should preferably be used within the above range.

Since the formazan metal complexes of the present invention exert satisfactory solubility in organic solvents, they are substantially not restricted to a specific organic solvent for coating on substrates along with organic dye compounds. Thus, to prepare the optical recording media of the present invention, TFP which is used frequently to prepare optical recording media and the following commonly used organic solvents other than TFP can be selectively used or, if necessary, appropriately used in combination; hydrocarbons such as pentane, hexane, cyclohexane, petroleum ether, petroleum benzine, isooctane, octane, benzene, toluene, and xylene; halogen compounds such as carbon tetrachloride, chloroform, 1,2-dichloroethane, 1,2-dibromoethane, trichloroethylene, tetrachloroethylene, chlorobenzene, bromobenzene, and á-dichlorobenzene; alcohols and phenols such as methanol, ethanol, 1-propanol, 2-propanol, 2,2,2-trifluoroethanol, 1-butanol, isobutyl alcohol, isopentyl alcohol, cyclohexanol, ethylene glycol, propylene glycol, 2-methoxy ethanol (methyl cellosolve), 2-ethoxy ethanol (ethyl cellosolve), phenol, benzyl alcohol, cresol, diethylene glycol, triethylene glycol, glycerine, and diacetone alcohol; ethers such as diethyl ether, diisopropyl ether, tetrahydrofuran, tetrahydropyran, 1,4-dioxane, anisole, 1,2-dimethoxyethane, diethylene glycol dimethyl ether, cyclohexyl-18-crown-6, methyl carbitol, and ethyl carbitol; ketones such as furfural, acetone, 1,3-diacetyl acetone, ethyl methyl ketone, and cyclohexanone; esthers such as ethyl acetate, butyl acetate, ethylene carbonate, propylene carbonate, and trimethyl phosphate; amides such as formamide, N-methyl formamide, N,N-dimethylformamide, and hexamethylphosphoric triamide; nitriles such as acetonitrile, propionitrile, succinonitrile, and benzonitrile; nitro compounds such as nitromethane and nitrobenzene; amines such as ethylene diamine, pyridine, piperidine, morpholine, and N-methylpyrrolidone; and sulfur-containing compounds such as dimethylsulfoxide and sulfolane.

Particularly, since the formazan metal complexes of the present invention have relatively-high solubility in TFP and easily-volatile organic solvents such as methyl cellosolve, ethyl cellosolve, and diacetone alcohol, they are substantially free of crystallization of organic dye compounds and metal complexes and free of inconsistency of thickness and surface of recording layers even when sequentially dissolved in the above organic solvents, coated on substrates, and dried. Most of the formazan metal complexes of the present invention well dissolve in non-halogen solvents, for example, cellosolves such as methyl cellosolve and ethyl cellosolve; alcohols such as methanol, diacetone alcohol, and isopropyl alcohol; and ketones such as ethyl methyl ketone and cyclohexanone. The above non-halogen solvents have the merit that they scarcely damage substrates and less pollute the environment when used for dissolving the formazan metal complexes of the present invention to coat on the substrates.

Commercialized substrates can be used in the present invention, and usually the substrates usable in the present invention can be processed with appropriate materials, for example, into discs, 12 cm in diameter and 0.6–1.2 mm in thickness, to suite to final use by the methods such as compression molding, injection molding, compression-injection molding, photopolymerization method (2P method), thermosetting integral method, and lightsetting integral method, depending on final use. The discs can be used singularly or plurally after appropriately attaching them together with adhesive sheets, etc. Examples of the materials for substrates are glasses, ceramics, and others such as plastics such as poly(methylmethacrylate), polycarbonate, polystyrene (styrene copolymer), polymethylpenten, polyether, polyolefin, polyimide, polyetherimide, polysulfone, polyethersulfone, polyarylate, polycarbonate/polystyrene alloy, polyestercarbonate, polyphthalatecarbonate, polycarbonateacrylate, non-crystalline polyolefin, methacrylate copolymer, diallylcarbonatediethylene-glycol, epoxy resin, and phenol resin, among which polycarbonate is frequently used. In the case of plastic substrates, concaves for expressing synchronizing-signals and addresses of tracks and sectors are usually transferred to the internal circle of the tracks of plastic substrates during the formation of the substrates.

The light-resistant improvers of the present invention are generally prepared into solutions of the above organic solvents in combination with organic dye compounds as light absorbents and coated to homogeneity over substrates to form a recording layer having a thickness of 10–1,000 nm, and preferably, 20–500 nm after drying. Prior to coating of the solutions, preliminary layers can be formed over the substrates to improve the protection and the adhesion ability of the substrates, if necessary. Materials for the preliminary layers are, for example, high-molecular substances such as ionomer resins, is polyamide resins, vinyl resins, natural resins, silicons, and liquid rubbers. In the case of using binders, the following polymers can be used alone or in combination in a weight ratio of 0.01–10 times of organic dye compound(s): Cellulose esters such as nitrocellulose, cellulose phosphate, cellulose sulfate, cellulose acetate, cellulose propionate, cellulose lactate, cellulose palmitate, and cellulose acetate/propionate; cellulose ethers such as methyl cellulose, ethyl cellulose, propyl cellulose, and butyl cellulose; vinyl resins such as polystyrene, poly(vinyl chloride), poly(vinyl acetate), poly(vinyl acetal), poly(vinylbutyral), poly(vinyl formal), poly(vinyl alcohol), and poly(vinyl pyrrolidone); copolymer resins such as styrene-butadiene copolymers, styrene-acrylonitrile copolymers, styrene-butadiene-acrylonitrile copolymers, vinyl chloride-vinyl acetate copolymers, and maleic anhydride copolymers; acrylic resins such as poly(methyl methacrylate), poly (methyl acrylate), polyacrylate, polymethacrylate, polyacrylamide, and polyacrylonitrile; polyesters such as poly(ethylene terephthalate); and polyolefins such as polyethylene, chlorinated polyethylene, and polypropylene.

Explaining the method for using the optical recording media according to the present invention, the optical recording media such as CD-Rs and DVD-Rs according to the present invention can write a variety of information at a relatively-high density by using laser beams, having wavelengths of around 600–830 nm, irradiated by semiconductor lasers such as those of AlGaInP, GaAsP, GaAlAs, InGaP, InGaAsP and InGaAlP; or YAG lasers combined with second harmonic generation inducing elements (SHG elements). To read out recorded information, laser beams with wavelengths identical to or slightly longer wavelengths than those used for writing information. As for the laser power for writing and reading information, in the optical recording media of the present invention, it is preferably set to a relatively-high level which exceeds the threshold of energy required for forming pits when used for writing information, while it is preferably set to a relatively-low level, i.e., a level below the threshold, when used for reading recorded information, although the laser power varies depending on the type and ratio of cyanine dyes used in combination with the light-resistant improvers of the present invention. Generally, the laser power can be controlled to a level of at least 1 mW, and usually 3–30 mW for writing; and to a level of below 1 mW, and usually 0.1–0.5 mW for reading. The recorded information is read out by using a light pick-up for detecting the change of the reflection light level or the transmission light level in the pits and the pit-less part on the recorded surface of optical recording media.

Since the optical recording media of the present invention can record information of characters, images, voices, and other digital data at a relatively-high density, they are extremely useful as recording media for professional and family use to record/backup and keep documents, data, and computer softwares. Particular examples of the kinds of industries and the forms of information, to which the optical recording media of the present invention can be applied, are as follows: Drawings of constructions and engineering works, maps, ledgers of loads and rivers, aperture cards, architectural sketches, documents of disaster protection, wiring diagrams, arrangement plans, information of news papers and magazines, local information, blueprints of productions for construction specifications, etc., which all relate to constructions and engineering works; blueprints, ingredient tables, prescriptions, product specifications, product price tables, part's lists, information for maintenance, case study files of accidents and troubles, manuals for claims, production schemes, technical documents, sketches, details, company's house-made product files, technical reports, analysis reports, etc., which all relate to manufacturing; customer's information, correspondent's information, company's information, contracts, informations of news papers and magazines, business reports, reports of company's credibility, records of stocks, etc., which all relate to sales; company's information, records of stocks, statistical documents, informations of news papers and magazines, contracts, customer's lists, documents of application/notification/licenses/authorization, business reports, etc., which all relate to financial; information of properties, sketches of constructions, maps, local information, information of news papers and magazines, contracts of lease, company's information, records of stocks, traffic information, information of correspondents, etc, which all relate to real properties and transportations; diagrams of writings and piping arrangements, documents of disaster protection, tables of operation manuals, documents of investigations, technical reports, etc., which all relate to electric and gas supplies; cartes, files of clinical histories and case studies, diagrams of medical care/institution relationships, etc., which all relate to medical fields; texts, collections of questions, educational documents, statistical information, etc., which all relate to private and preparatory schools; scientific papers, records in academic societies, monthly reports of researches, research data, documentary records and indexes thereof, etc., which all relate to universities, colleges, and research institutes; inspection data, literatures, patent publications, weather maps, analytical records of data, customer's files, etc., which all relate to information; case studies on laws; membership lists, history notes, records of works/products, competition data, data of meetings/congresses, etc., which all relate to organizations/associations; sightseeing information, traffic information, etc., which all relate to sightseeing; indexes of homemade publications, information of news papers and magazines, who's who files, sport records, telop files, scripts for broadcastings, etc., which all relate to mass communications and publishers; and maps, ledgers of roads and livers, fingerprint files, resident cards, documents of application/notification/license/authorization, statistical documents, public documents, etc., which all relate to government offices. Particularly, the write-once type optical recording media of the present invention can be advantageously useful for storing records of cartes and official documents which must not be deleted or rewritten intentionally, and used as electric libraries for art galleries, libraries, museums, broadcasting stations, etc.

As a rather specific use, the optical recording media of the present invention can be used to edit and prepare compact discs, digital video discs, laser discs, MDs (a mini disc as information recording system using photomagnetic disc), CDVs (a laser disc using compact disc), DATs (an information recording system using magnetic tape), CD-ROMs (a read-only memory using compact disc), DVD-ROMs (a read-only memory using digital video disc), DVD-RAMs (a writable and readable memory using digital video disc), digital photos, movies, computer graphics, publishing products, broadcasting programs, commercial messages, video softwares, audio softwares, game softwares, etc.; and used as external program recording means for large size of computers and car navigation systems.

Hereinbefore described are the application examples of the light-resistent improvers of the present invention to optical recording media as a use thereof, however, the use of the present invention should not be restricted only to such optical recording media. In addition to the above use in optical recording media, the light-resistent improvers of the present invention can be advantageously used, for example, in photo polymerizable compositions, photos, dye lasers, electroluminescence devices, panels and filters for information displaying apparatuses, plastics, rubbers, papers, clothes, woods, paints, dyes, brightening agents, scintillator, reagents for fluorescence analysis, etc. More particularly, when applied to organic dye compounds used as photosensitizers for polymerizing polymerizable compounds using light irradiation, chemical sensitizers to regulate photosensitization efficiency during exposure of silver prints, and as laser-active substances in dye lasers, the light-resistant improvers of the present invention effectively improve the light resistance of the organic dye compounds and control their sensitivity to light.

Since most of the formazan metal complexes of the present invention have absorption maxima in visible region, they are advantageously useful, for example, as dyes for dying clothes and photosensitizers for polymerizing polymerizable compounds by exposing to visible light. If necessary, by combining with one or more other light absorbents capable of absorbing light in ultraviolet and infrared regions, the formazan metal complexes of the present invention can be used in clothes in general and others including building/bedding/decorating products such as drapes, laces, casements, prints, venetian blinds, roll screens, shutters, shop curtains, blankets, thick bedquilts including comforters, peripheral materials for thick bedquilts, covers for thick bedquilts, cottons for thick bedquilts, bed sheets, cushions, pillows, pillow covers, cushions, mats, carpets, sleeping bags, tents, interior finishes for cars, and window glasses; sanitary and health goods such as paper diapers, diaper covers, eyeglasses, monocles, and lorgnettes; internal base sheets, linings, and materials for shoes, wrappers, materials for umbrellas, parasols, stuffed toys, lighting devices; filters, panels and screens for image displaying devices such as television receivers and personal computers which use cathode-ray tubes, liquid crystal displays, electroluminescent displays, and plasma displays; sunglasses, sunroofs, sun visors, Pet bottles, refrigerators, plastic greenhouses, lawns, optical fibers, prepaid cards, and peeping windows of electric ovens and other types of ovens. When used as wrapping-, injecting-, and enclosing-materials for the above products/articles, the formazan metal complexes of the present invention prevent living bodies and products/articles from troubles and discomforts induced by environmental lights such as natural- and artificial-lights or even lower the troubles and discomforts, and furthermore they can advantageously regulate the color, tint, and appearance, and adjust the light reflected from or passed through the products/articles to a desired color balance.

As described above, the formazan compounds and tautomers thereof are advantageously useful as intermediates for effectively producing the formazan metal complexes of the present invention. The formazan compounds and tautomers thereof, which have carboxyl group and/or sulfonyl group as $\phi1$, $\phi2$ and/or $\phi3$ in Formula 1, have satisfactory absorbency to optical semiconductors which are mainly composed of zinc oxide, titanium oxide, etc., and effectively absorb light in a wide range of visible light so that they can be advantageously used as optical absorbents in solar batteries which convert solar light to electric energy by using optical semiconductors.

The following examples describe the preferred embodiments of the present invention:

EXAMPLE 1

Formazan Compound

Five grams of 2-pyridylhydrazine and 5.0 g of 3-pyridylaldehyde were dissolved in 100 ml methanol and reacted at 60° C. for two hours under stirring conditions, and then the reaction mixture was cooled to 10° C. or lower, admixed with 50 ml of water, and allowed to stand at the same temperature for another 30 min under stirring conditions. Thereafter, the resulting crystal was collected by filtering, sufficiently washed with water and methanol, and dried by heating at 65° C. to obtain 7.4 g of a colorless needle-like crystal of the hydrazone compound represented by Chemical Formula 42.
Chemical Formula 42:

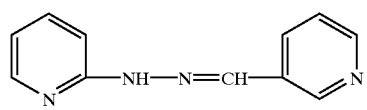

One hundred milliliters of a mixture solution of 1,4-dioxane and methanol (=3:2 by volume) were placed in a reaction vessel, admixed with 0.93 g of aniline and 2.0 g of the hydrazone compound represented by Chemical Formula 42 obtained in the above, further admixed with 2.5 ml of concentrated hydrochloric acid and 5 ml of water under stirring conditions, and then cooled to 0–3° C. While keeping at the temperature, 5 ml of an aqueous solution containing 0.72 mg of sodium nitrite were added to the mixture drop by drop over about 20 min, then admixed with 10 ml of an aqueous solution containing 1.38 g sodium hydroxide drop by drop over about 20 min, and the resulting mixture was stirred for two hours at the same temperature. Thereafter, the reaction mixture was mixed with 100 ml of water, followed stirring for 30 min. The resulting crystal was collected by filtering, sufficiently washed with water and methanol, and dried by heating at 65° C. to obtain 1.6 g of a dark-red crystal of the formazan compound of the present invention, represented by Chemical Formula 2.

Conventional measurement revealed that the formazan compound of this example had a melting point of 167–171° C. and showed an absorption maximum at a wavelength of 461 nm when measured in methylene chloride.

EXAMPLE 2

Formazan Compound

A hydrazone compound represented by Chemical Formula 43 was obtained similarly as in Example 1 except that 2-pyridylhydrazine in Example 1 was replaced with 5-trifluoromethyl-2-pyridylhydrazine.
Chemical Formula 43:

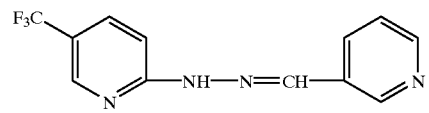

One hundred and fifty milliliters of a mixture solution of formamide and 1,4-dioxane (=1:2 by volume) were placed in a reaction vessel, admixed with 5.3 g of the hydrazone compound obtained in the above and 2.4 g of 4-cyanoaniline, then admixed with 5 ml of concentrated hydrochloric acid, 7 ml of triethylamine, and 10 ml of water. While keeping at 0–5° C. under stirring conditions, 6 ml of an aqueous solution containing 1.44 g of sodium nitrite were added to the above mixture drop by drop over about 30 min, and the resulting mixture was stirred for two hours at the same temperature. Thereafter, to the reaction mixture was added 150 ml of water, followed by stirring for 30 min. The resulting crystal was collected by filtering, sufficiently washed with water and methanol, and dried by heating at 65° C. to obtain 1.0 g of a dark-red crystal of the formazan compound represented by Chemical Formula 23.

Conventional measurement revealed that the formazan compound of this example had a melting point of 70–73° C. and showed an absorption maximum at a wavelength of 472 nm when measured in methylene chloride.

EXAMPLE 3

Formazan Compound 7.7 g of 5-nitro-2-pyridylhydrazine and 5.5 g of 2-pyridylaldehyde were dissolved in 150 ml methanol and allowed to react at 50° C. for two hours under stirring conditions. To the reaction mixture was added 50 ml of water, and the resulting mixture was cooled to ambient temperature. The formed crystal was collected by filtering, sufficiently washed with water and methanol, and dried by heating at 65° C. to obtain 9.9 g of a yellow needle-like crystal of the hydrazone compound represented by Chemical Formula 44.

Chemical Formula 44:

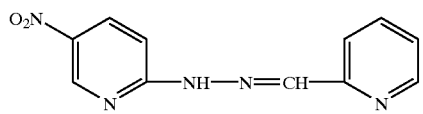

One thousand milliliters of N,N-dimethylformamide was placed in a reaction vessel, admixed with 4.8 g of the hydrazone compound obtained in the above and 3.1 g of 2,5-dimethoxyaniline, and then admixed with 5 ml of concentrated hydrochloric acid, 6 ml of triethylamine, and 10 ml of water. While keeping at 0–5° C. under stirring conditions, 6 ml of an aqueous solution containing 1.44 g of sodium nitrite were added to the mixture drop by drop over about 30 min. Thereafter, the resulting mixture was further stirred for one hour at the same temperature, mixed with 12 ml of acetic acid, and 500 ml of water, followed by stirring for 20 min. The resulting crystal was collected, sufficiently washed with water and methanol, and dried by heating at 65° C. to obtain 1.0 g of a dark-red crystal of the formazan compound represented by Chemical Formula 20.

Conventional measurement revealed that the formazan compound of this example had a melting point of 139–141° C. and showed an absorption maximum at a wavelength of 422 nm when measured in methylene chloride.

EXAMPLE 4

Formazan Compound

A hydrazone compound, represented by Chemical Formula 45, was obtained similarly as in Example 3 except that 2-pyridylaldehyde in Example 3 was replaced with 2-furaldehyde.

Chemical Formula 45:

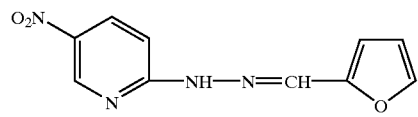

One hundred and fifty milliliters of a mixture solution of 1,4-dioxane and N,N-dimethylformamide (=2:1 by volume) were placed in a reaction vessel, admixed with 4.7 g of the hydrazone compound, represented by Chemical Formula 45, obtained in the above and 2.2 g of 3-methylaniline, then admixed with 5 ml of concentrated hydrochloric acid and 10 ml of water and cooled to 0. While keeping at the temperature, the resulting mixture was mixed with 6 ml of an aqueous solution containing 1.4 g of sodium nitrite drop by drop over about 20 min, followed by stirring for another two hours. Thereafter, the formed crystal was collected by filtering, sufficiently washed with water and methanol, and dried by heating at 65° C. to obtain 6.0 g of a dark-brown crystal of the formazan compound represented by Chemical Formula 35.

Conventional measurement revealed that the formazan compound of this example had a melting point of 159–160° C. and showed an absorption maximum at a wavelength of 467 nm when measured in methylene chloride.

EXAMPLE 5

Formazan Metal Complex

Forty milliliters of methanol were placed in a reaction vessel and admixed with 2.0 g of the formazan compound, represented by Chemical Formula 2, obtained by the method in Example 1. Under stirring conditions and while keeping at 50° C., the mixture was admixed with 40 ml of methanol solution containing 1.0 g of nickel acetate tetrahydrate drop by drop over about 30 min, followed by stirring at the same temperature for another 30 min. Thereafter, the resulting mixture was mixed with 80 ml of water, and then cooled to 10° C. or lower, followed by filtering to collect the formed crystal, sufficiently washing the crystal with water and methanol, and heating to dry the resultant crystal at 65° C. to obtain 0.9 g of a purple crystal of nickel complex having the formazan compound represented by Chemical Formula 2 as a ligand.

Conventional measurement revealed that the formazan metal compound of this example had a melting point of 290–295° C. and showed an absorption maximum at a wavelength of 599 nm when measured in methylene chloride. The absorption spectrum of the formazan metal compound was shown in FIG. 1.

EXAMPLE 6

Formazan Metal Complex

Forty milliliters of methanol were placed in a reaction vessel and admixed with 1.0 g of the formazan compound represented by Chemical Formula 23, obtained by the method in Example 2. Under stirring conditions and while keeping at 60° C., the above mixture was admixed with 20 ml of methanol solution containing 0.5 g of nickel acetate tetrahydrate drop by drop over about 30 min, followed by stirring at the same temperature for another four hours. Thereafter, the resulting mixture was mixed with 80 ml of water, followed by filtering to collect the formed crystal, sufficiently washing the crystal with water and methanol, and heating to dry the resultant crystal at 65° C. to obtain 0.8 g of a black crystal of nickel complex having the formazan compound represented by Chemical Formula 23 as a ligand.

Figure 2:
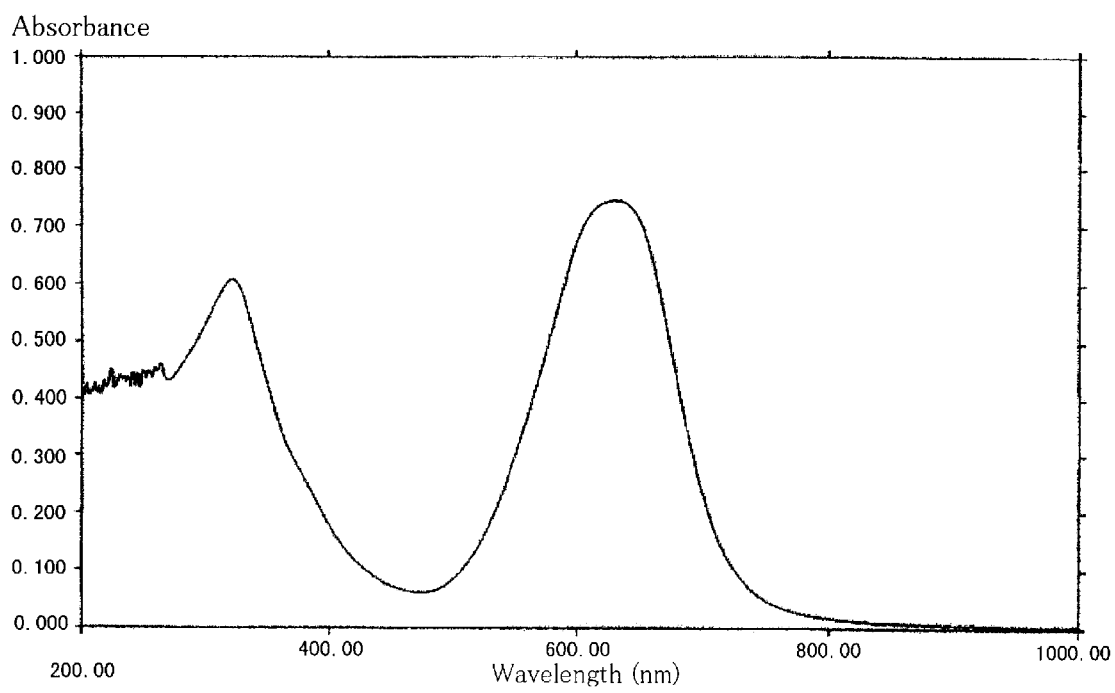
FIG. 2 is an absorption spectrum of another formazan metal complex according to the present invention.

Conventional measurement revealed that the formazan metal compound of this example had a melting point of 220–230° C. and showed an absorption maximum at a wavelength of 629 nm when measured in methylene chloride. The absorption spectrum of the formazan metal compound was shown in FIG. 2.

EXAMPLE 7

Formazan Metal Complex

Fifty milliliters of methanol were placed in a reaction vessel and admixed with 0.5 g of the formazan compound, represented by Chemical Formula 20, obtained by the method in Example 3. Under heating and refluxing conditions, the mixture was admixed with 5 ml of an aqueous solution containing 0.18 g of nickel acetate tetrahydrate under heat-refluxing conditions, and then refluxed by heating for another one hour. The reaction mixture was cooled, and the formed crystal was collected by filtering, sufficiently washed with water and methanol, and dried by heating at 65° C. to obtain 0.3 g of a liver crystal of nickel complex having the formazan compound represented by Chemical Formula 20 as a ligand.

Figure 3:
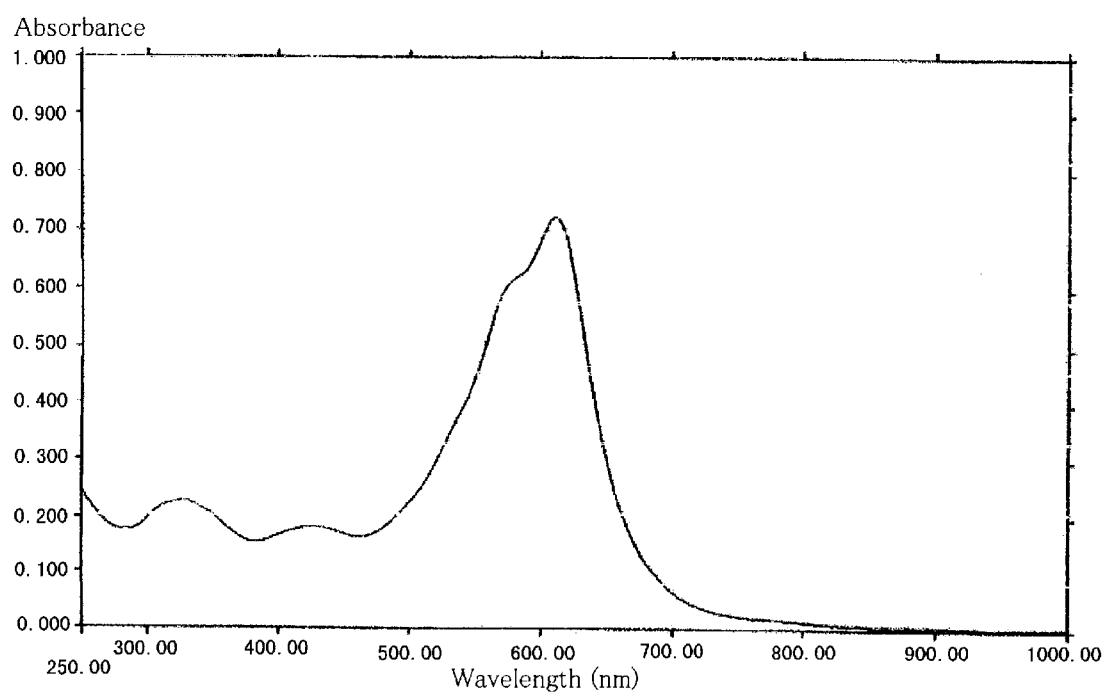
FIG. 3 is an absorption spectrum of the other formazan metal complex according to the present invention.

Conventional measurement revealed that the formazan metal compound of this example had a melting point of 230–231° C. and showed an absorption maximum at a wavelength of 611 nm when measured in methylene chloride. The absorption spectrum of the formazan metal compound was shown in FIG. 3.

EXAMPLE 8

Formazan Metal Complex

Sixty milliliters of methanol were placed in a reaction vessel and admixed with 1.0 g of the formazan compound, represented by Chemical Formula 35, obtained by the method in Example 4. Under heat-refluxing conditions, the mixture was admixed with 8 ml of an aqueous solution containing 0.43 g of nickel acetate tetrahydrate, and then refluxed by heating for another 90 min. The reaction mixture was cooled, and the formed crystal was collected by filtering, sufficiently washed with water and methanol, and dried by heating at 65° C. to obtain 0.9 g of a black-purple crystal of nickel complex having the formazan compound represented by Chemical Formula 35 as a ligand.

Figure 4:
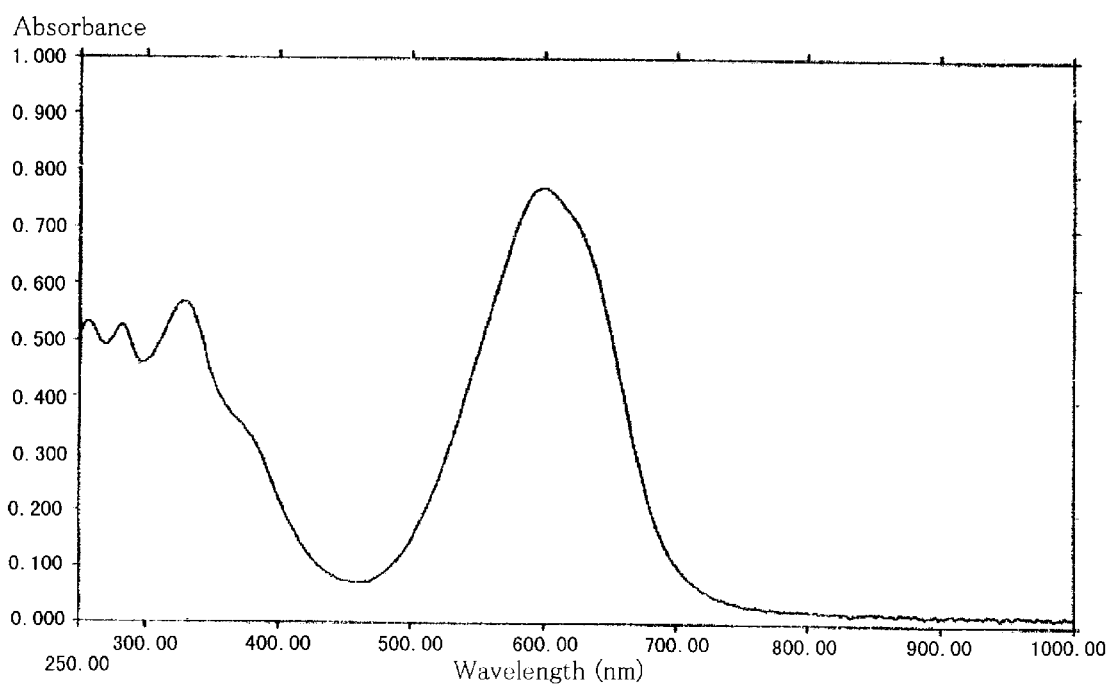
FIG. 4 is an absorption spectrum of another formazan metal complex according to the present invention.

Conventional measurement revealed that the formazan metal compound of this example had a melting point of 212–215° C. and showed an absorption maximum at a wavelength of 670 nm when measured in methylene chloride. The absorption spectrum of the formazan metal compound was shown in FIG. 4.

Although there exist some differences in production conditions and yields, the formazan metal complexes of the present invention, as well as those having the formazan compounds, represented by Chemical Formula 1 to 41, as ligands, can be all prepared by the methods in Examples 1 to 8 or in accordance therewith.

EXAMPLE 9

Improvement of Light Resistance of Cyanine Dye

To 3 ml of TFP were added as a test specimen 2 mg of a nickel complex having, as a ligand, any one of the formazan compounds as shown in Table 1, and the cyanine dyes represented by Chemical Formulae 46 and 47 as light absorbents in respective amounts of 10 mg and 5 mg, followed dissolving the contents by energizing with 5-min ultrasonication at ambient temperature. Then, in accordance with conventional manner, a prescribed amount of the solution was dropped on either side of a glass substrate, 5 cm×5 cm, which had been ground, followed by rotating the substrate at a rate of 1,000 rpm for one minute to homogeneously coat the solution on the substrate and drying the coated solution with sequential blows of hot air and cool air.

Chemical Formula 46:

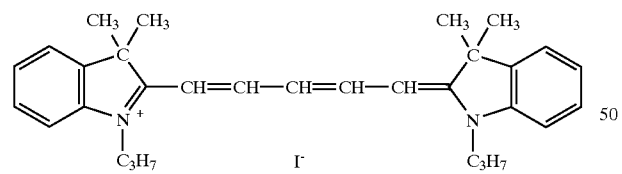

Chemical Formula 47:

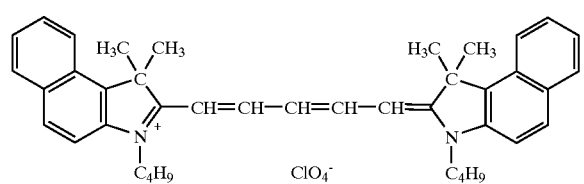

The resulting glass substrates coated with the light absorbents were measured for transmittance ($T_0$) at a wavelength of 700 nm in a usual manner. Then, the substrates were fixed to a position 7 cm apart form a 500 W xenon lamp and exposed with the light of the lamp for 25 min while blowing cool air to the substrates, and then remeasured for transmittance (T) at a wavelength of 700 nm. The transmittance of T and $T_0$ for each formazan metal complex were substituted for the Equation 1 to calculate the residual percentage (%) of each cyanine dye. In parallel, there provided a system using, as a light-resistant improver, a conventional nickel complex having any one of the formazan metal complexes represented by Chemical Formulae 48 and 49 in place of the above formazan metal complexes of the present invention; and a system with no light-resistant improver. These systems as controls were treated similarly as above (hereinafter called "control 1", "control 2", and "control 3"). The results are in Table 1.

Chemical Formula 48:

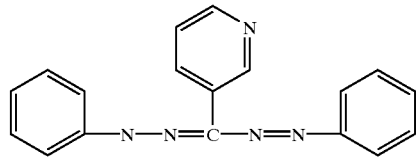

Chemical Formula 49:

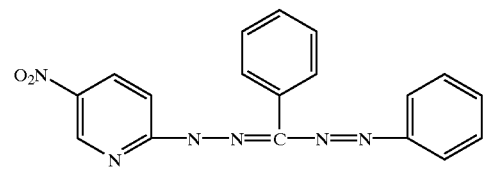

Equation 1:

$$\text{Residual percentage of photosensitive dye (\%)} = \frac{100 - T}{100 - T_0} \times 100$$

TABLE 1

| Ligand | Central atom | Absorption maximum (nm) | Molecular extinction coefficient ε | Solubility (mg/ml) TFP | *Et-cellosolve | Residual percentage (%) | Remarks |
|---|---|---|---|---|---|---|---|
| Chemical Formula 2 | Nickel | 599 | 25,300 | 36.3 | 11.9 | 94.4 | Present invention |
| Chemical Formula 3 | Nickel | 597 | 27,500 | 50.3 | 44.2 | 98.6 | Present invention |

TABLE 1-continued

| Ligand | Central atom | Absorption maximum (nm) | Molecular extinction coefficient ε | Solubility (mg/ml) TFP | Solubility (mg/ml) *Et-cellosolve | Residual percentage (%) | Remarks |
|---|---|---|---|---|---|---|---|
| Chemical Formula 8 | Nickel | 626 | 52,600 | 42.8 | 2.1 | 98.4 | Present invention |
| Chemical Formula 20 | Nickel | 611 | 90,400 | 63.0 | 22.7 | 97.6 | Present invention |
| Chemical Formula 22 | Nickel | 600 | 45,600 | 102.2 | 72.2 | 99.4 | Present invention |
| Chemical Formula 23 | Nickel | 629 | 43,500 | 72.2 | 46.2 | 99.8 | Present invention |
| Chemical Formula 24 | Nickel | 603 | 35,900 | 97.7 | 57.8 | 99.6 | Present invention |
| Chemical Formula 40 | Nickel | 626 | 54,800 | 11.5 | 3.8 | 97.2 | Present invention |
| Chemical Formula 48 | Nickel | 776 | 9,500 | 1.9 | 0.5 | 85.4 | Control 1 |
| Chemical Formula 49 | Nickel | 583 | 85,800 | 56.4 | 1.2 | 66.5 | Control 2 |
| Free of light-resistant improver | | | | — | — | 60.1 | Control 3 |

Note: The symbol "*" means ethyl cellosolve.

As shown in the results of measurement in Table 1, in control 3, which was free of light-resistant improver, about 40% of the cyanine dye had changed with only 25-min exposure and became incapable of exerting its inherent optical property. While in the systems with the formazan metal complexes of the present invention and controls 1 and 2 with conventional nickel complexes, more than 66% of the initial cyanine dyes still remained intact. Comparing the systems of the present invention with controls 1 and 2, the remaining percentage of the cyanine dyes in control 1 or 2 was at most 85%, while those of the systems of the present invention were far exceeding controls 1 and 2, i.e., over 94% of the cyanine dyes remained intact. Particularly, the formazan metal complexes, having the formazan compounds, represented by Chemical Formulae 22, 23 and 24, as ligands, showed an outstandingly-high light-resistant improvement, i.e., over 99% of the cyanine dyes remained intact. These results indicate that the formazan metal complexes of the present invention are advantageously used as light-resistant improvers for organic dye compounds including cyanine dyes.

EXAMPLE 10

Solubility of Formazan Metal Complex

Nickel complexes, having any one of the formazan compounds in Table 1 as a ligand, were measured for solubility in TFP and ethyl cellosolve at 20° C. according to conventional manner. In parallel, conventional nickel complexes, having the formazan compounds represented by Chemical Formulae 48 and 49 as ligands, were measured for solubility similarly as above. The results are all in Table 1.

As found in the results of measurement in Table 1, the solubility in ethyl cellosolve of the nickel complexes as controls was at most about 1.2 mg/ml, while those of the formazan metal complexes of the present invention marked far exceeding high-solubility, i.e., at least 2.1 mg/ml. As in TFP, the nickel complexes as controls only showed solubility of about 2–21 mg/ml, while most of the formazan metal complexes of the present invention tested showed far exceeding high-solubility, i.e., solubility of at least 36 mg/ml. In the field of optical recording media, ethyl cellosolve is expected for use as a solvent that less pollutes the environment. TFP is a representative organic solvent used for coating polymethine dyes such as cyanine dyes on substrates for optical recording media. The fact, that the formazan metal complexes of the present invention showed the aforesaid outstanding solubilities in ethyl cellosolve and TFP, indicates that the light-resistant improvers of the present invention can be advantageously used in optical recording media such as CD-Rs and DVD-Ds which use polymethine dyes. As evident from the results of measurement in Table 1, the formazan metal complexes of the present invention used for measurement can be also useful as light absorbents that absorb visible light because of their relatively-high molecular extinction coefficient.

EXAMPLE 11

Optical Recording Medium

The cyanine dyes, represented by Chemical Formulae 46 and 47, as light absorbents, were added to TFP to give final concentrations of 1.5% (w/w) respectively, and further admixed with any one of the formazan metal complexes of the present invention, represented by Chemical Formulae 2, 3, 8, 20, 22, 23, 24 and 40, to give a concentration of 0.3% (w/w), followed by ultrasonically dissolving the contents. The resulting solution was in a usual manner homogeneously coated in a rotatory manner over one side of a polycarbonate disc substrate, 12cm in diameter and 1.2 mm in thickness, which concaves for expressing synchronizing-signals and addresses of tracks and sectors had been transferred to the track's internal circuit, and dried to form a recording layer, 100 nm in thickness. Thereafter, the resulting substrate was deposited in vaccuo with gold to form a reflection layer, 100 nm in thickness, to be attached closely on the surface of the recording layer, and the reflection layer was homogeneously coated in a rotatory manner with "UNIDIC SD1700", as a known ultraviolet ray hardening resin commercialized by Dainippon Ink and Chemicals, Inc., Tokyo, Japan, and irradiated to form a protection layer to be attached closely on the surface of the reflection layer. Thus, eight types of optical recording media were prepared.

Figure 5:
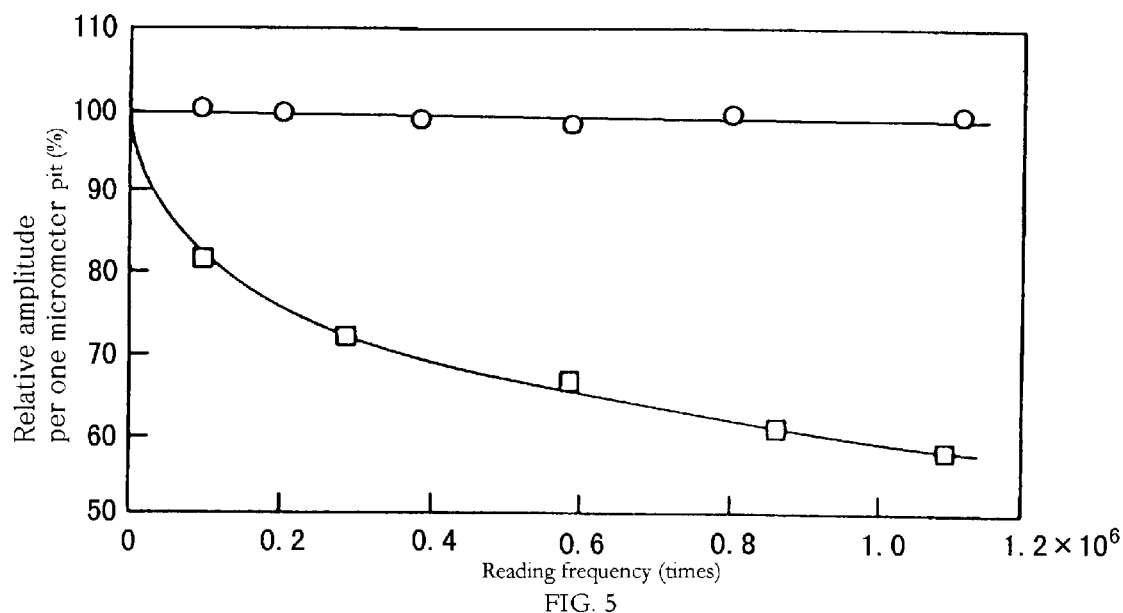
FIG. 5 is a figure of the effect of one of the light-resistant improvers according to the present invention on a CD-R.

In accordance with the method as disclosed in "*Nihon-Kagakukai-Shi*" (Japan Chemical Association), by Shuichi Yanagisawa, No. 10, pp. 1,141–1,143 (1992), using a semi-conductor laser beam with an oscillation wavelength of 780 nm, a square wave was written in the CD-Rs obtained in the above with a recording power of 8 mW, and then the recorded data was successively read out with a reading power of 0.7 mW, and the amplitude per 1 μm pit of the read out square-waves was read out at time intervals by using an oscilloscope, where the rotation speed of disc was set to a linear velocity of 1.4 m/sec so as to make the frequency of output signal 720 kHz for recording and reading). For the read-out amplitude, the ratio (%) of the amplitude after a prescribed-repetition time of reading against that of the initial amplitude was calculated and used as an index of the light-resistant improvement of cyanine dyes in optical recording media. In parallel, there provided as a control a system with no formazan metal complex of the present invention and treated similarly as above. FIG. 5 shows the result of measurement of a CD-R using, as a light-resistant improver, the formazan metal complex of the present invention having the formazan compound represented by Chemical Formula 2 as a ligand. In FIG. 5, the solid line containing a symbol "○" shows a time-dependent change of amplitude for the CD-R with a light-resistant improver, while the solid line containing a symbol "□" shows that for a CD-R with no light-resistant improver.

As evident from the results in FIG. 5, the amplitude of the CD-R of control clearly decreased as the reading time increased, and lowered to about 60% to the initial amplitude after a reading time of 1×10⁶. In the case of the CD-Rs using the formazan metal complexes of the present invention, the change in amplitude was negligible even after a reading time of 1×10⁶ of reading recorded information. As compared with control, the CD-Rs of the present invention showed a significantly-high output signal level and made no reading error. Careful electron-microscopic observation of the recording surface of the CD-Rs in this example detected no crystal of cyanine dye and metal complex. As the data of measurement was not shown, the CD-Rs using formazan metal complexes other than the one represented by Chemical Formula 3 showed superior results similarly as of the formazan metal complex represented by Chemical Formula 3. These results indicate that, when used in optical recording media, the light-resistant improvers of the present invention effectively inhibit undesirable change in polymethine dyes such as cyanine dyes, induced by the exposure of light such as reading light without substantially deteriorating preferable light properties of the polymethine dyes; and the formazan metal complexes of the present invention have satisfactory compatibility with the polymethine dyes.

The CD-Rs in this example have a recording capacity of over 600 MB (megabytes) and can record information of documents, images, voices, and digital data at a relatively-high density by using a light pick-up of a laser beam with a wavelength of 780 nm. It is no use saying that the CD-Rs in this example have satisfactory durability required of optical recording media in general so that once recorded information can be accurately read out more than 10 years even when repeatedly read out and exposed to environmental light for a relatively-long period of time.

POSSIBILITY OF INDUSTRIAL APPLICABILITY

As described above, the present invention was made based on the creation of novel formazan metal complexes and their industrially useful properties. When applied to organic dye compounds including cyanine dyes, the formazan metal complexes of the present invention outstandingly improve the light resistance and effectively inhibit undesirable changes such as deterioration, fading, discoloration, and denaturation of organic dye compounds induced by exposure of light without substantially deteriorating their desirable properties. Comparing with conventional formazan metal complexes, the formazan metal complexes of the present invention have far superior solubility in organic solvents and have greatly-high compatibility with polymethine dyes such as cyanine dyes.

Thus, the light-resistant improvers containing the formazan metal complexes of the present invention can be very advantageously applicable to those, in which the change in properties of organic dye compounds should be avoided, for example, optical recording media, optical sensitizers, chemical sensitizers, dye lasers, electroluminescent devices, panels and filters for information-displaying apparatuses, plastics, rubbers, papers, clothes, woods, paints, dyes, brightening agents, scintillator, and reagents for fluorescent analysis. Particularly, since the optical recording media containing the formazan metal complexes of the present invention substantially do not make reading error of recorded information even when read out repeatedly and stored for a relatively-long period of time, they have extensively-wide applicability as media which have satisfactory storage-stability and can record information of characters, images, voices, and other digital data at a relatively-high density.

In addition, the formazan metal complexes of the present invention can be advantageously used in a variety of products as optical sensitizers, chemical sensitizers, dyes, and light absorbents. The formazan metal complexes of the present invention, which have such advantageous usefulness, can be easily produced in desired amounts through a step of reacting with appropriate metal salts the formazan compounds or tautomers thereof of the present invention.

The present invention having such outstanding effects and function is a significant invention that will greatly contribute to this art.

What is claimed is:

1. A formazan compound represented by Formula 1 or a tautomer thereof:

Formula 1:

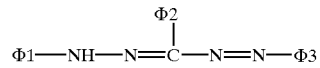

wherein Formula 1, Φ1 represents a pyridine ring which has a substituent; Φ2 represents a pyridine ring, furan ring or branched alkyl group, said pyridine ring and said furan ring optionally have a substituent; and Φ3 represents an aromatic ring which optionally has a substituent.

2. A formazane metal complex, which has solubility of at least 2 mg/ml in ethyl cellosolve at 20° C. and comprises as a ligand (Fz) a formazan compound represented by Formula 1 or a tautomer thereof:

Formula 1:

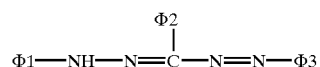

wherein Φ1 in Formula 1 represents a pyridine ring which has a substituent; Φ2 in Formula 1 represents a pyridine ring, furan ring or branched alkyl group, said pyridine ring and said furan ring optionally have a substituent; and Φ3 in Formula 1 represents an aromatic ring which optionally has a substituent.

3. An optical recording medium, which comprises the formazan metal complex of claim 2.

4. The optical recording medium of claim 3, which comprises one or more appropriate polymethine dyes along with the formazan metal complex.

5. The optical recording medium of claim 4, wherein said one or more polymethine dyes has an amidinium ion chromophore.

6. The formazan metal complex of claim 2, which is represented by Formula 2 comprising as a ligand (Fz) a formazan compound represented by Formula 1 or a tautomer thereof, and being a complex of said $F_z$ and a bivalent metal (M):

Formula 2:

$$F_{zm} \cdot M \cdot Xn$$

wherein in Formula 2, m is a number of $F_z$ which binds to M; X is a counter ion for a metal complex; and n is a number of X for keeping the balance of electric charge in the metal complex.

7. A light-resistant improver, which comprises the formazan metal complex of claim 2.

8. A light absorbent, which comprises the formazan metal complex of claim 2.

9. The light absorbent of claim 8, which comprises one or more appropriate polymethine dyes along with the formazan metal complex.

10. The light absorbent of claim 9, wherein at least one of said one or more polymethine dyes has an amidinium ion chromophore.

11. A process for producing the formazan metal complex of claim 2, which comprises a step of reacting a formazan compound represented by the Formula 1 or a tautomer thereof with an appropriate metal salt.

* * * * *

UNITED STATES PATENT AND TRADEMARK OFFICE
CERTIFICATE OF CORRECTION

PATENT NO. : 6,645,594 B1
DATED : November 11, 2003
INVENTOR(S) : Yano et al.

It is certified that error appears in the above-identified patent and that said Letters Patent is hereby corrected as shown below:

<u>Title page,</u>
Item [22], delete "Jan. 6, 2000" and insert therefor -- June 1, 2000 --.

Signed and Sealed this

Thirteenth Day of April, 2004

JON W. DUDAS
*Acting Director of the United States Patent and Trademark Office*